United States Patent [19]

Sugimoto

[11] Patent Number: 4,841,230
[45] Date of Patent: Jun. 20, 1989

[54] DEVICE FOR MEASURING MOISTURE CONTENT IN GRAINS

[75] Inventor: Naoto Sugimoto, Fukuroi, Japan

[73] Assignee: Shizuoka Seiki Co., Ltd., Fukuroi, Japan

[21] Appl. No.: 239,911

[22] Filed: Sep. 2, 1988

[30] Foreign Application Priority Data

Sep. 4, 1987 [JP] Japan .................. 62-135977[U]

[51] Int. Cl.⁴ .................................. G01N 27/04
[52] U.S. Cl. ........................................ 324/65 R
[58] Field of Search ............ 324/65 R, 65 P, 61 R, 324/61 P; 73/73, 866

[56] References Cited

U.S. PATENT DOCUMENTS 1,826,247 10/1931 Heppenstall .............. 324/65 R
3,047,801 7/1962 Dietert ...................... 324/65 P
3,646,437 2/1972 Nutter ....................... 324/65 R

FOREIGN PATENT DOCUMENTS

212055 11/1960 Austria ...................... 324/65 R
115947 9/1981 Japan ........................ 324/65 R
 52848 3/1982 Japan ........................ 324/65 R
104848 6/1982 Japan ........................ 324/65 R
110947 7/1982 Japan ........................ 324/65 R
62-35254 3/1987 Japan .
890208 12/1981 U.S.S.R. ................... 324/65 R Primary Examiner—Tom Noland
Attorney, Agent, or Firm—Armstrong, Nikaido, Marmelstein, Kubovcik & Murray

[57] ABSTRACT

A device for measuring moisture content in grains has a base supporting plate, a movable supporting plate pivotally mounted on the base supporting plate. A first roller electrode is rotatably mounted on the base supporting plate and a second roller electrode is rotatably mounted on the movable supporting plate adjacent the first roller electrode. A spring is provided between the base and movable supporting plates so as to press the second roller electrode against the first roller electrode.

2 Claims, 7 Drawing Sheets

DEVICE FOR MEASURING MOISTURE CONTENT IN GRAINS

BACKGROUND OF THE INVENTION

The present invention relates to a device for measuring moisture content in a grain such as a grain of rice and more particularly to an improved spring assembly provided in the device for adjusting pressure between a pair of roll electrodes which crushes a grain and measures the moisture content therein.

Japanese Utility Model Laid Open No. 62-35254 discloses a device for measuring moisture content where a pair of roll electrodes is provided to crush a sample grain one by one, and to detect the electric resistance in the grain between the electrodes. The detected electric resistance is converted to a voltage signal representing the moisture content in the grain.

In the device, a shaft of each roll electrode is supported by two bearings. A spring assembly comprising a coil spring is provided in each bearing of the shaft of one of the electrodes. The coil spring urges the electrode toward the other electrode so as to automatically adjust the pressure between the electrodes despite the variation of the size of the grain. Accordingly, the moisture content can be accurately measured.

However, in order to obtain a necessary pressure between the pair of electrodes, a coil spring having a large spring constant must be employed. Therefore the spring assembly inevitably becomes large, resulting in increase of the size of the measuring device. Furthermore, a complicated operation of adjusting the balance between both spring assemblies must be performed, causing high cost.

SUMMARY OF THE INVENTION

The object of the present invention is to provide a simple and compact spring assembly for applying pressure to a pair of roll electrodes wherein the pressure can be easily adjusted.

According to the present invention, there is provided a device for measuring moisture content in grains, comprising a conveyer for conveying grains, a base supporting plate secured to a wall of the conveyer, a movable supporting plate pivotally mounted on the base supporting plate, a first roller electrode rotatably mounted on the base supporting plate, a second roller electrode rotatably mounted on the movable supporting plate adjacent the first roller electrode, a spring provided between the base and movable supporting plates so as to press the second roller electrode against the first roller electrode, a motor mounted on the base supporting plate, a gear train operatively connected between the motor and the first and second electrodes, for driving the electrodes.

In an aspect of the invention, the movable supporting plate is pivotally mounted on a shaft of a gear in the gear train.

These and other objects and features of this invention will become understood from the following description with reference to the accompanying drawings.

DETAILED DESCRIPTION OF THE PREFERRED EMBODIMENT

Figure 1:
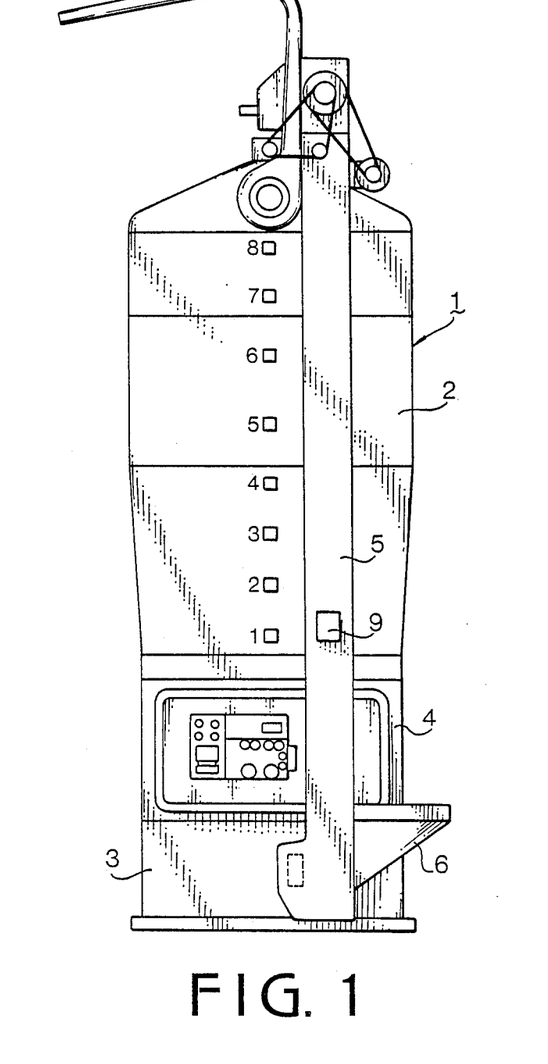
FIG. 1 i an elevational view of a grain dryer to which the present invention is applied.
Figure 2:
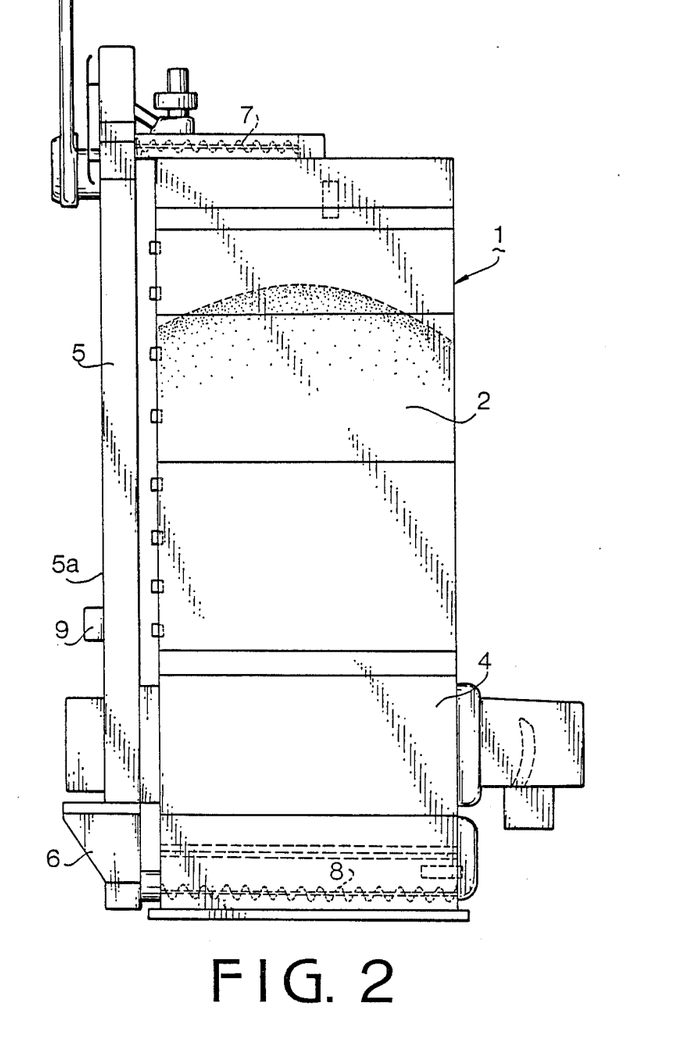
FIG. 2 is a side view of the grain dryer.

Referring to FIGS. 1 and 2, a grain dryer 1 to which the present invention is applied has a grain storing section 2, a grain collecting section 3 and a drying section 4. Grains K which are fed to a hopper 6 provided at a lower portion of the dryer 1 are conveyed by a bucket conveyer 5 to an upper conveyer 7. The upper conveyer 7 conveys the grains to the central part of the dryer and lets them uniformly fall in the storing section 2. The grains are dried in the drying section 4 and fall on a lower conveyer 8 which conveys the grains to a lower end portion of the bucket conveyer 5. Thus, the drying cycle is repeated. A moisture content detector 9 for measuring the moisture content in grains is attached to a lower portion of an outer side wall 5a of the conveyer 5.

Referring to FIGS. 3 to 6, the moisture content detector 9 comprises a grain sample collector 17, a pair of roller electrodes 31 and 34 and a gear train for driving the collector and the electrodes. The collector 17 is mounted on a base supporting plate 10 securely attached to the side wall 5a of the conveyer 5 at a position where an inlet opening 11 is formed. The base plate 10 has a rising wall 10a perpendicular to the side wall 5a, and having bosses 13a and 16a for respectively supporting shafts 13 and 16, which will later be described. A motor 12 for driving the gear train is mounted on the rising wall 10a.

Figure 3:
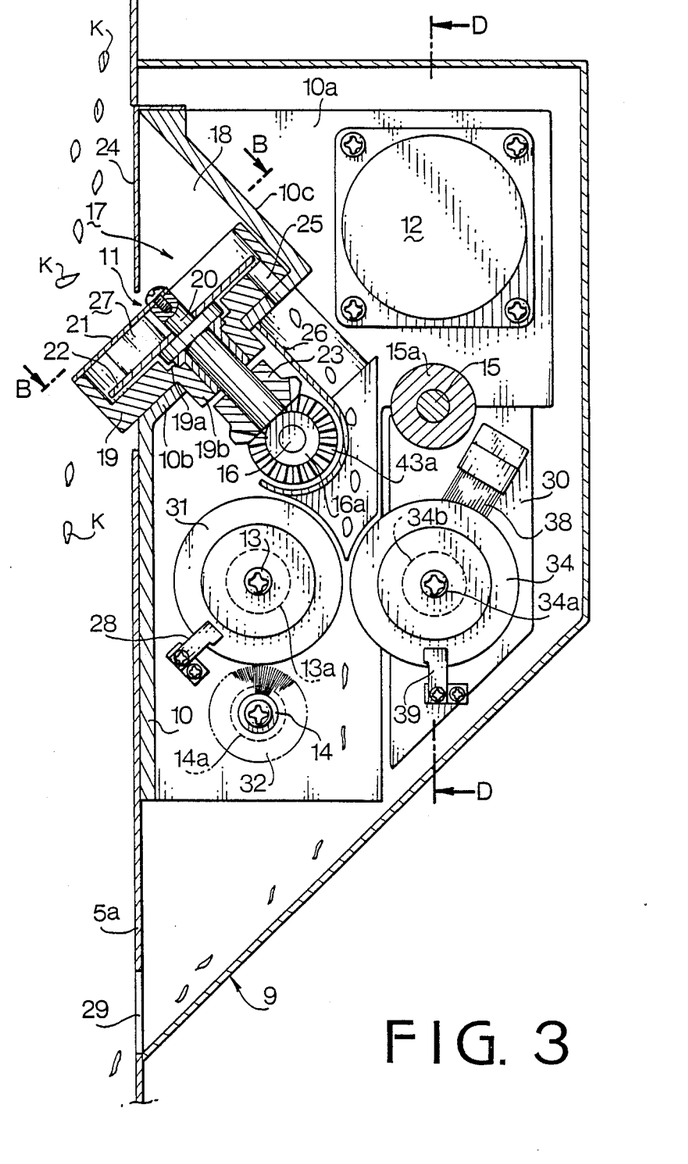
FIG. 3 is a sectional view of a moisture content detector, taken along a line A—A of FIG. 5.
Figure 5:
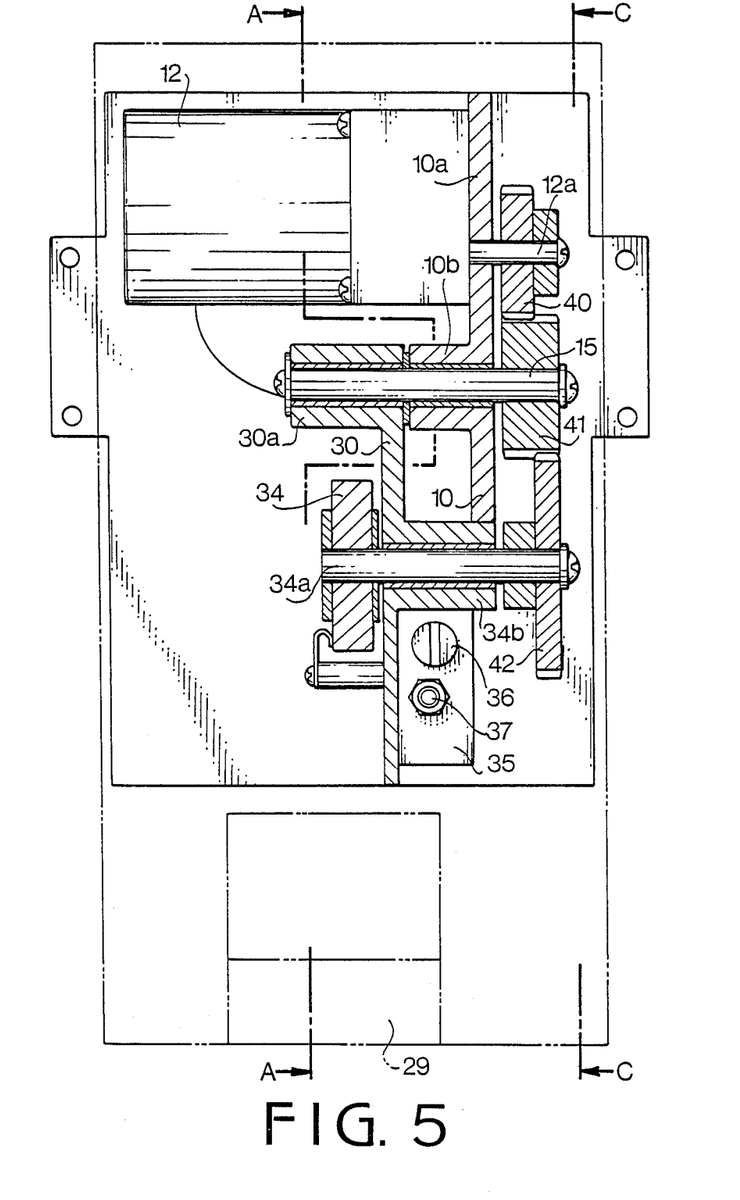
FIG. 5 is sectional view taken along a line D—D of FIG. 3.

The base supporting plate 10 further has a curved wall 10c encircling the periphery of an arc-rimmed wall 10b and slanting inward so as to overlook the opening 11 and the arc-rimmed wall 10b. The walls 10b and 10c define a collecting chamber 18 in which the sample collector 17 is provided. The collector comprises a collector cylinder 19 the bottom 19a of which is in contact with the arc-rimmed wall 10b, protruding into the conveyer 5 so as to receive grains falling from buckets. Bottom 19a of the cylinder 19 is formed with a boss 19b which is inserted into an opening formed in a center of the arc-rimmed wall 10b. A shaft 20 to which a bevel gear 23 is fixedly mounted at a lower end is rotatably mounted in the boss 19b.

Figure 4:
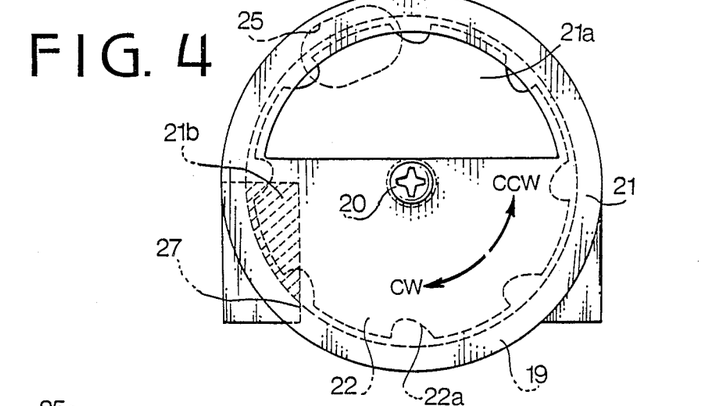
FIG. 4 is a sectional view taken along a line B—B of FIG. 3.

On an upper end of the shaft 20, a circular shutter 21 having a semicircular opening 21a as shown in FIG. 4 is securely mounted. A circular plate 22 having a plurality of recesses 22a (FIG. 4) on the periphery thereof is also securely mounted on the shaft 20 below the shutter 21. A part of the opening 11 above the cylinder 19 is closed by a screen 24 so as to prevent the grains K from directly entering the chamber 18. The grains K which entered the cylinder 19 through the opening 21a of the shutter 21 are admitted one by one through the recess 22a into a bore 25 bored through the bottom 19a of the cylinder 19 and the arc-rimmed wall 10b. The grain K is guided to the pair of roll electrodes by a curved guide plate 26. A projection 21b (FIG. 4) having an arcuated periphery corresponding to a part of the periphery of the shutter 21 is provided so as to enable the excessive grain in a space 27 between the shutter 21 and the plate 22 to be easily discharged when the opening 21a of the shutter 21 is at a specific position.

An outlet 29 is formed in the side wall 5a at a lower portion of the side wall 5a so as to discharge the crushed grains.

The left roll electrode 13 is provided below the guide plate 26 adjacent the conveyer 5. The electrode 13 is securely mounted on the shaft 13 which is supported with the boss 13a of the wall 10. A brush 28 is in contact with the electrode 31 to obtain an electric resistance signal. A roll brush 32 fixedly mounted on the shaft 14 is disposed below the electrode 31.

As shown in FIG. 5, a movable supporting plate 30 having a supporting boss 30a is pivotally mounted on the shaft 15 securely mounted on the base supporting plate 10. Opposite to the supporting boss 30a, a boss 34b wherein a shaft 34a is fitted is formed on the plate 30. The shaft 34a carries the right roll electrode 34 contacted with a brush 39 for obtaining an electric resistance signal. A cleaning brush 39 is provided above the electrode 34.

Figure 6:
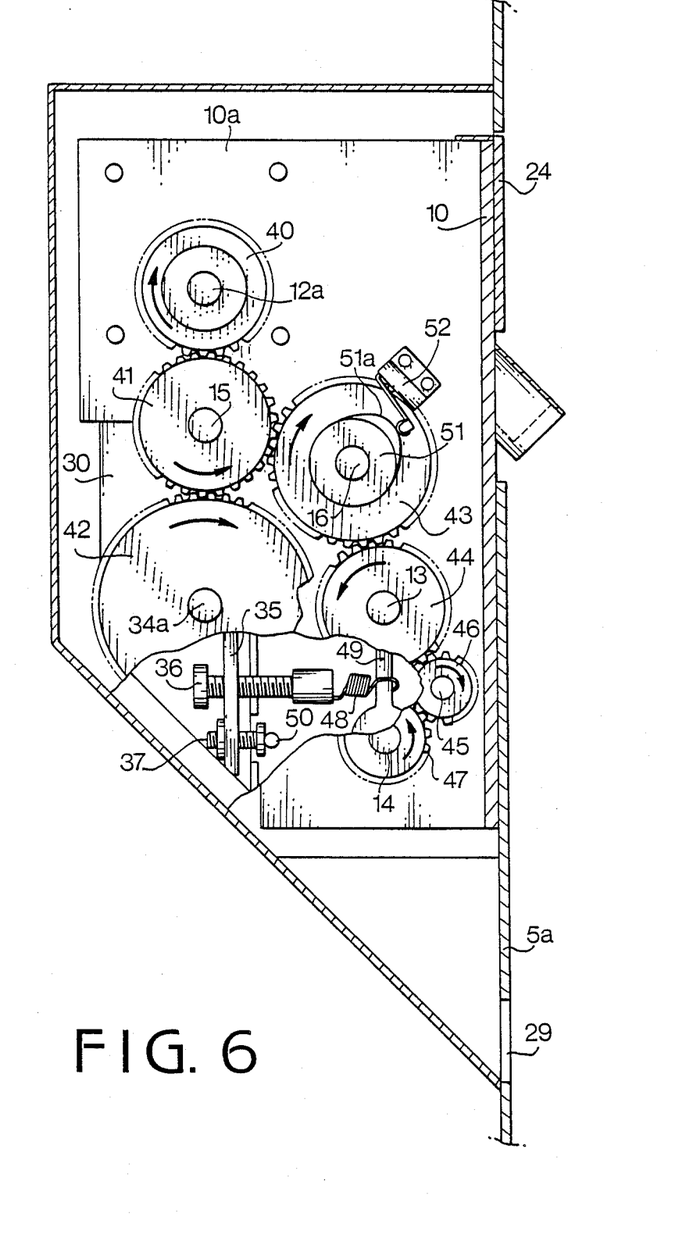
FIG. 6 is a partially cutaway sectional view taken along a line C—C of FIG. 5.

A plate 35 is perpendicularly securely attached to the supporting plate 30 under the boss 34b as shown in FIGS. 5 and 6. An adjusting screw 36 is mounted in the plate 35 and a coil spring 48 is provided between the screw and a holding bar 49 formed between the bosses 13a and 14a on the base plate 10. Thus, the spring 48 draws the electrode carrier 30 toward the base plate 10, thereby pressing the right roll electrode 34 against the electrode 37. The spring load can be adjusted by turning the adjusting screw 36. In order to adjust a minimum gap between the electrodes 31 and 34, an adjusting screw 37 which abuts against a stopper 50 formed on a partition 10a is also screwed in the plate 35.

A gear train for driving the sample collector 17 and the roll electrodes 31 and 34 will now be described with reference to FIGS. 5 and 6. A gear 40 securely mounted on a shaft 12a of the motor 12 meshes with a gear 41 rotatably mounted on the shaft 15. The gear 41 in turn meshes with a gear 42 fixedly mounted on the shaft 34a of the right roll electrode 34 and with a gear 43 securely mounted on the shaft 16 supported on the base 10. The shaft 16 further carries a bevel gear 43a securely mounted thereon at the other side of the wall 10a. The gear 43a is in mesh with the bevel gear 23 of the collector 17, thereby rotating the shaft 20 and hence the shutter 21 and the plate 22 when the motor 12 is driven.

The gear 43 is further in mesh with a gear 44 fixedly mounted on the shaft 13 and which in turn meshes with a gear 47 securely mounted on the shaft 14 of the roll brush 32. Thus, the electrodes 31 and 34 are rotated in opposite directions.

A rotary sleeve 51 having a cam 51a is securely mounted on the shaft 16 at an outer side of the gear 43. The cam 51a turns on a limit switch 52 which in turn stops the motor 12 so as to restrict the rotation of the grain sample collector 17.

The operation of the moisture content detector 9 will be described hereinafter with reference to FIGS. 7a to 7d.

Figure 7A:
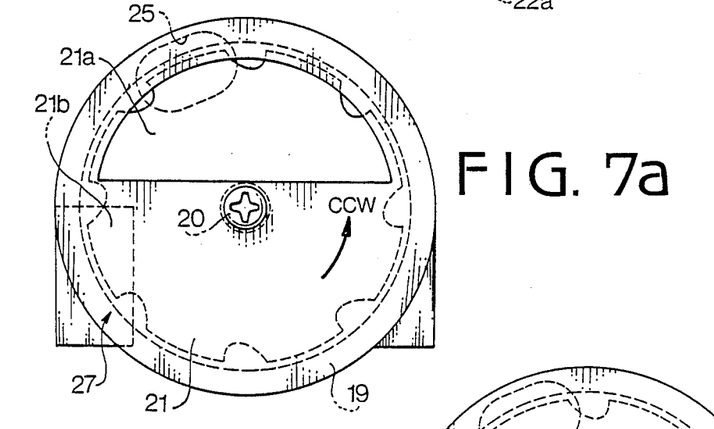
FIGS. 7a to 7d are diagrams explaining the operation of a grain sample collector.

FIG. 7a shows the grain sample collector 17 at a standby position where the motor 12 is not yet operated. The opening 21a of the shutter 21 is situated in the collecting chamber 18 behind the screen 24. At the same time the projection 21b on the underside of the shutter 21 is positioned to close the space 27. As a result, grains K are prevented from falling into the collecting cylinder 19.

Figure 7B:
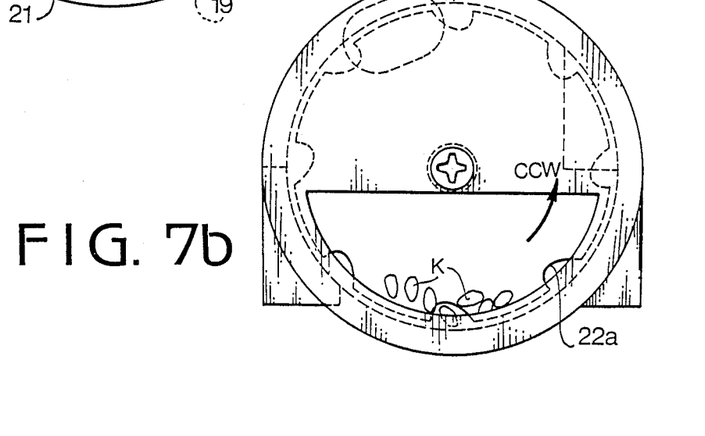

When the motor 12 is driven for a predetermined period of time, the shaft 20 is counterclockwisely rotated through the gears 40, 41, 43, 43a and 23 to a sampling position shown in FIG. 7b. The shutter 21 is positioned so that the opening 21 openes to the conveyer 5. Thus, some of the grains K falling through the conveyer 5 enter the cylinder 19 through the opening 21a and accumulate therein. As the shaft 20 continues to rotate in the counterclockwise direction to a measuring position shown in FIG. 7c, the accumulated grains K are fed in the bore 25 through the recesses 22a one by one. The grains K then slide down the guide plate 26 and fall into the gap between the roll electrodes 31 and 34.

Figure 7C:
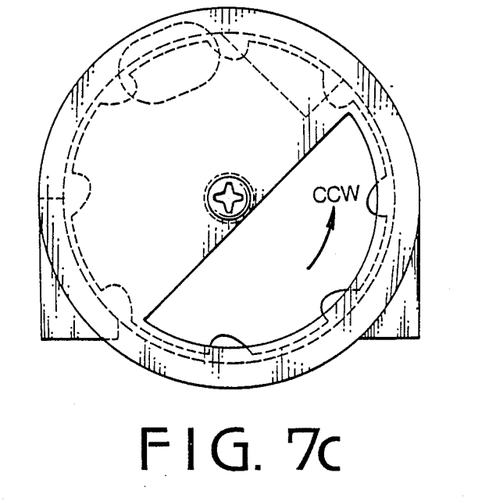

At the same time, the roll electrodes 31 and 34 are rotated simultaneously in the opposite directions through the gears 40, 41, 43 and 44 and by the gears 40, 41 and 42, respectively. The grains K enter between the electrodes one by one and are crushed by them. Signals representing electric resistance between the roll electrodes 31 and 34 are applied to a control section (not shown) through the brushes 28a and 39. The signal is converted into a voltage signal representing a moisture content which is displayed or used as a data for controlling the drying level of the grains K. The crushed grain is discharged through the sample outlet 29.

Figure 7D:
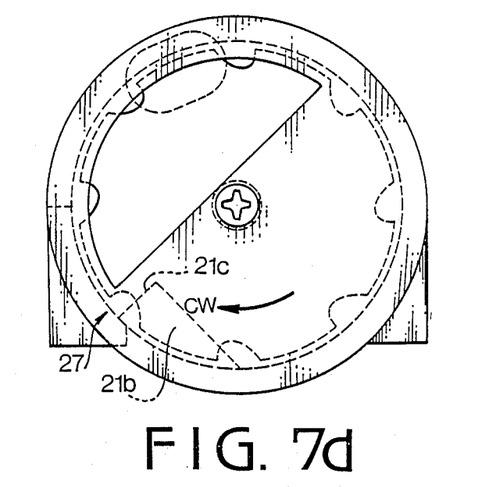

Hereafter, the motor 12 is driven so as to rotate the shaft 20 in the clockwise direction to a discharging position shown in FIG. 7d, where the cylinder 19 is emptied for the next sampling operation. Excessive grains K in the space 27 are pushed upward with a surface 21c of the projection 21b as the shutter 21 is rotated. As a result, the grains K are discharged through the opening 21a. The shaft 20 is further rotated in the clockwise direction to the initial position where the motor 12 stops. The operation is thus repeated as described at predetermined intervals until the drying operation of the grain dryer 1 is terminated.

During the operation, since the spring 48 is provided between the base supporting plate 10 and the movable plate 30 pivotally mounted on the base plate 10, the plate 30 serves as a lever, with the shaft 15 being a fulcrum. Accordingly, a spring having a smaller spring constant than in a conventional device can be used, so that the diameter of the spring 48 can be made small. In addition, a single coil spring is sufficient, and a complicated operation of adjusting the pressure between the electrodes while keeping the balance of the shaft supporting one of the electrodes becomes unnecessary.

In a modification of the present invention, the tension coil spring may be replaced with a compression spring so disposed as to directly urge the movable supporting plate 30 toward the base supporting plate 10. Another shaft may be provided on the wall 10a in addition to the shaft 15 so as to rotatably support the plate 30 independently.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A device for measuring moisture content in grains, comprising:

a base supporting plate secured to a wall of the device;

a movable supporting plate pivotally mounted on the base supporting plate;

a first roller electrode rotatably mounted on the base supporting plate;

a second roller electrode rotatably mounted on the movable supporting plate adjacent the first roller electrode;

a spring provided between the base and movable supporting plates so as to press the second roller electrode against the first roller electrode;

a motor mounted on the base supporting plate;

a gear train operatively connected between the motor and the first and second electrodes, for driving the electrodes.

2. The device according to claim 1 wherein the movable supporting plate is pivotally mounted on a shaft of a gear in the gear train.

* * * * *